US00PP25758P3

(12) United States Plant Patent
Bornstein

(10) Patent No.: US PP25,758 P3
(45) Date of Patent: Jul. 28, 2015

(54) ***GYPSOPHILA* PLANT NAMED 'PEARLS GINGA WAY'**

(50) Latin Name: ***Gypsophila paniculata* L.**
Varietal Denomination: Pearls Ginga Way

(71) Applicant: M.D. Gypsophila Breeding Ltd, Negev (IL)

(72) Inventor: Menachem Bornstein, Holon (IL)

(73) Assignee: Selecta Cut Flowers S.A.U., Barcelona (ES)

( * ) Notice: Subject to any disclaimer, the term of this patent is extended or adjusted under 35 U.S.C. 154(b) by 186 days.

(21) Appl. No.: 13/987,018

(22) Filed: Jun. 25, 2013

(65) Prior Publication Data

US 2014/0380534 P1 Dec. 25, 2014

(51) Int. Cl.
*A01H 5/00* (2006.01)

(52) U.S. Cl.
USPC ..... Plt./354

(58) Field of Classification Search
USPC ..... Plt./354
See application file for complete search history.

*Primary Examiner* — Susan McCormick Ewoldt
(74) *Attorney, Agent, or Firm* — James M. Weatherly; Barbara Campbell; Cochran Freund & Young LLC

(57) ABSTRACT

A new *Gypsophila* plant particularly distinguished by having vigorous growth and early flowering; large, full, pure white flowers of excellent quality year round, forming a rich inflorescence; good yield of long stems with a medium weight, stable and upright stems; good weather tolerance; performs well outdoors; low susceptibility to die-back; and good vase life, is disclosed.

2 Drawing Sheets

Genus and species: *Gypsophila paniculata* L.
Variety denomination: 'Pearls Ginga Way'.

BACKGROUND OF THE NEW PLANT

The present invention comprises a new and distinct variety of *Gypsophila*, botanically known as *Gypsophila paniculata* L., and hereinafter referred to by the variety name 'Pearls Ginga Way'. 'Pearls Ginga Way' originated from a crossing between the proprietary female *Gypsophila* variety 'BL-MD-F-56' (unpatented) and the male *Gypsophila* variety 'BL-MD-M-189' (unpatented) in April 2009 in Negev, Israel.

Seeds were obtained from the cross of 'BL-MD-F-56'× 'BL-MD-M-189' and sown. Plants were then grown for evaluation. A plant line was selected in August 2009 in Negev, Israel and named 'Pearls Ginga Way'. In September 2009 'Pearls Ginga Way' was first vegetatively propagated in Negev, Israel by side branch cuttings. 'Pearls Ginga Way' was found to reproduce true to type in successive generations of asexual propagation via side branch cuttings.

CROSS REFERENCE TO RELATED APPLICATIONS

Plant Breeder's Rights for 'Pearls Ginga Way' were applied for in Europe on Oct. 25, 2012, Application No. 2012/2341 and in Colombia on Jan. 2, 2013, Application No. A131792. 'Pearls Ginga Way' has not been made publicly available or sold more than one year prior to the filing date of this application.

SUMMARY

The following are the most outstanding and distinguishing characteristics of this new variety when grown under normal horticultural practices in Negev, Israel.

1. Vigorous growth and early to flower;
2. Large, full, pure white flowers of excellent quality year round, forming a rich inflorescence;
3. Good yield of long stems with a medium weight;
4. Stable and upright stems;
5. Low need for supplementary lighting;
6. Good weather tolerance;
7. Performs well outdoors;
8. Low susceptibility to die-back; and
9. Good vase life.

DESCRIPTION OF THE PHOTOGRAPHS

This new *Gypsophila* plant is illustrated by the accompanying photographs. The photographs are of a plant twelve-weeks from planting grown in an open field in Negev, Israel in November, 2012. The colors shown are as true as can be reasonably obtained by conventional photographic procedures.

Figure 1:
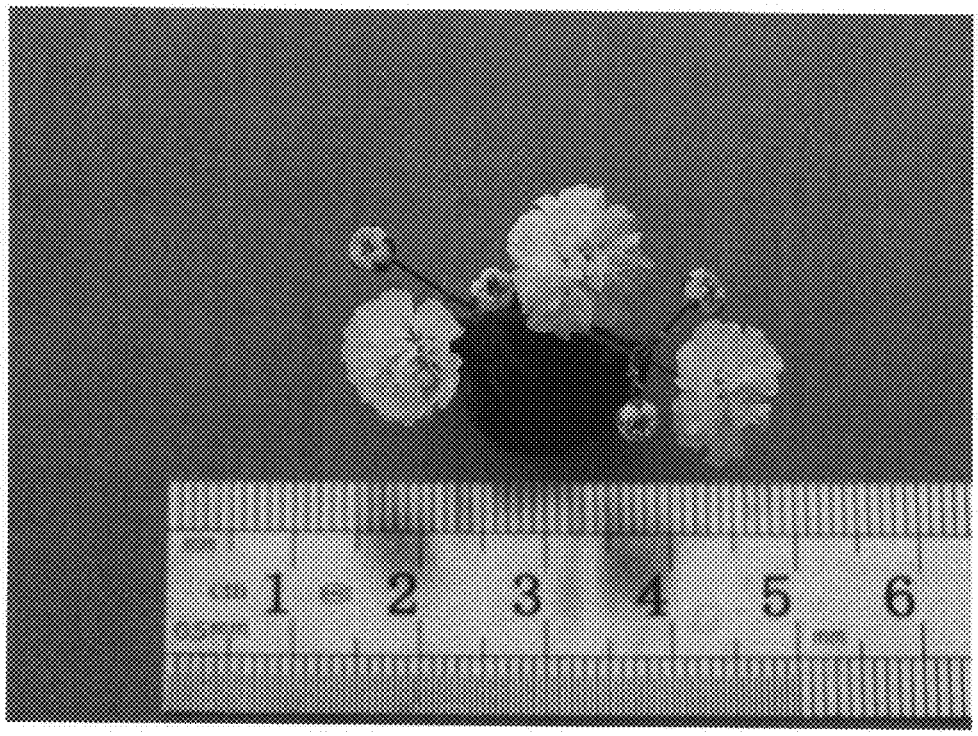
Figure 2:
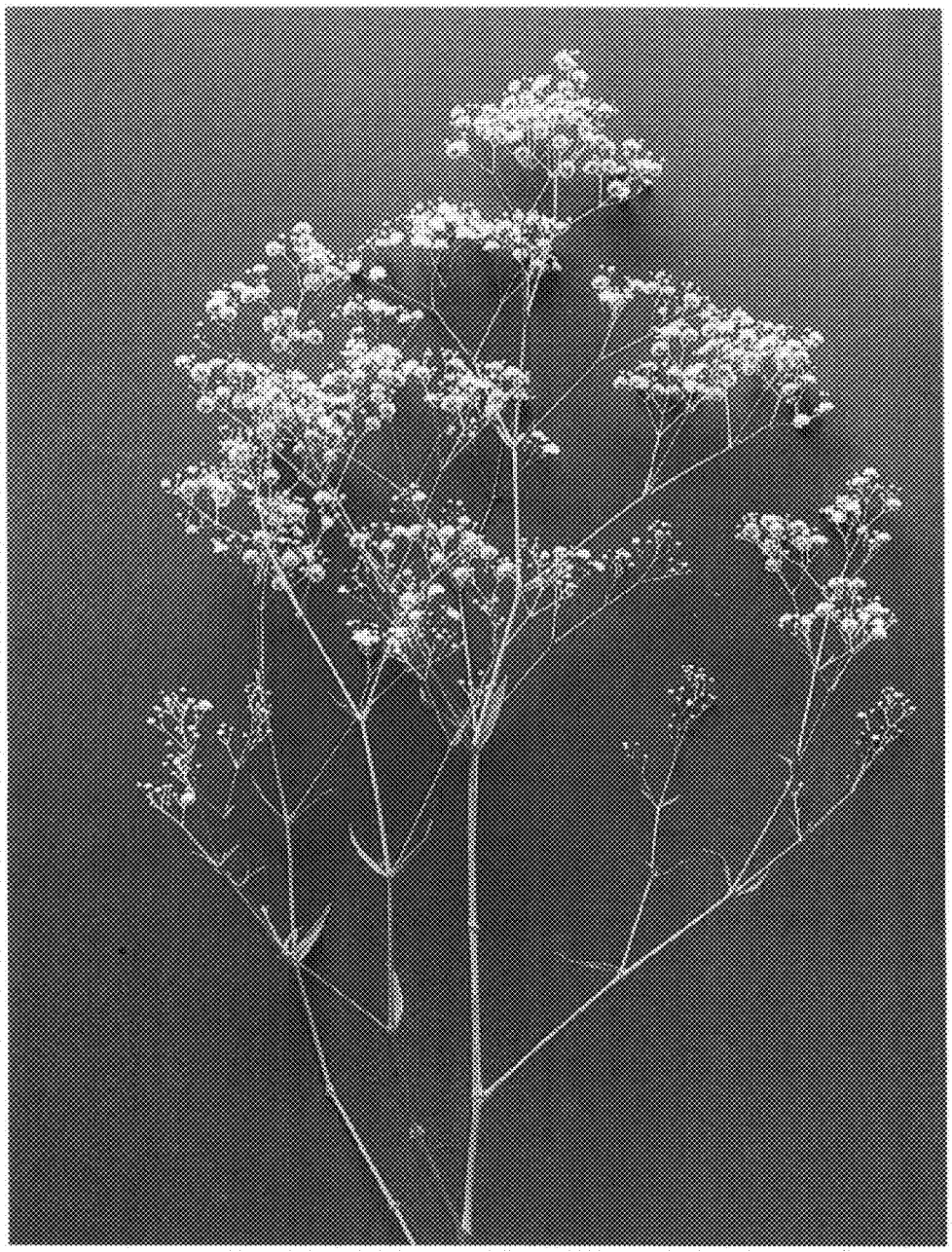

FIG. 1 shows a close-up of the flowers of the plant.
FIG. 2 shows the flowering stem of the plant.

DESCRIPTION OF THE NEW VARIETY

The following detailed descriptions set forth the distinctive characteristics of 'Pearls Ginga Way'. The data which define these characteristics were collected in Negev, Israel in the summer of 2012. Data was collected on plants ten weeks after planting. Color references are to The R.H.S. Colour Chart of The Royal Horticultural Society of London (R.H.S.) (version unknown).

Classification:
*Family*.—Caryophyllaceae.
*Botanical*.—*Gypsophila paniculata* L.
*Common name*.—Baby's Breath.
*Denomination*.—'Pearls Ginga Way'.

Parentage:
*Female parent*.—Proprietary line 'BL-MD-F-56' (unpatented).
*Male parent*.—Proprietary line 'BL-MD-M-189' (unpatented).
Plant:
*Form*.—Upright, shrub type.
*Habit*.—Perennial.
*Plant height*.—100.0 cm.
*Plant width*.—80.0 cm.
*Flowering habit*.—Year round in periodic flushes depending on growing conditions.
*Time to produce a finished flowering plant*.—4 weeks of rooting, plus one week of hardening, plus 8 to 12 weeks between planting and flowering depending on weather condition and cultivation.
*Propagation type*.—Vegetative by side branch cuttings.
*Time to initiate roots*.—2 to 3 weeks; plant fully rooted and ready for planting within 5 weeks.
*Root description*.—Light brown, woody spike main root with branched fibrillary secondary roots.
Flowering stems:
*Quantity per plant*.—7 to 9.
*Color*.—RHS 147C (Yellow-green).
*General description*.—Panicle.
*Stem strength*.—Stable.
*Length*.—80.0 cm.
*Diameter*.—50.0 cm.
*Internodes length*.—3.5 cm to 4.0 cm at stem base.
*Texture*.—Glabrous.
Leaves:
*Arrangement*.—Opposite.
*Shape*.—Lanceolate.
*Apex*.—Acute.
*Base*.—Wedge-shaped (Cuneate).
*Margin*.—Entire.
*Color*.—Immature leaf: Upper surface: RHS 137A (Green). Lower surface: RHS 137B (Green). Mature leaf: Upper surface: RHS: 137A (Green). Lower surface: RHS: 137B (Green).
*Length*.—7.5 cm to 8.0 cm.
*Width*.—1.2 cm to 1.3 cm.
*Texture*.—Fine pubescent.
*Venation pattern*.—Parallel.
*Venation color*.—Upper surface: RHS 137A (Green). Lower surface: RHS 137B (Green).
Flowers:
*Inflorescence type*.—Compound cymes with numerous flowers; panicle shaped.
*Flowering season*.—Year round naturally under 12 hours and above light duration.
*Lastingness of individual flowers on the plant*.—10 to 12 days.
*Lastingness of the flowers as a cut flower*.—10 to 12 days.
*Flower width*.—0.9 cm to 1.0 cm.
*Flower depth*.—0.6 cm.
*Flower shape*.—Oblate consisting of many petals (double type).
*Fragrance*.—Typical to *Gypsophila*.
*Number of inflorescences per plant*.—7 to 9.
*Number of flowers per inflorescence*.—Hundreds.
Inflorescence:
*Length* (*height*).—80.0 cm.
*Diameter*.—50.0 cm.
Pedicel:
*Length*.—0.6 cm to 0.8 cm.
*Diameter*.—0.1 cm.
*Strength*.—Stable.
*Texture*.—Glabrous.
*Color*.—RHS 147C (Yellow-green).
Peduncle:
*Length*.—80.0 cm.
*Diameter*.—0.6 cm to 0.7 cm at basal part.
*Texture*.—Glabrous.
*Color*.—RHS 147C (Yellow-green).
Flower buds: At opening.
*Color*.—RHS 155A (White).
*Shape*.—Oblate.
*Length*.—0.4 cm.
*Diameter*.—0.3 cm.
Petals:
*Arrangement*.—Pompon.
*Quantity*.—40 to 50 per flower.
*Shape*.—Spathulate.
*Apex*.—Emarginated; wavy.
*Base*.—Cuneate.
*Margin*.—Entire.
*Size*.—Length: 0.4 cm. Width: 0.2 cm.
*Color*.—When opening: Upper and lower surfaces: RHS 155A (White). Fully opened: Upper and lower surfaces: RHS 155D (White).
*Surface texture*.—Upper and lower surfaces: Glabrous.
Sepals:
*Arrangement*.—Cup shaped.
*Quantity*.—5 to 7.
*Shape*.—Lanceolate.
*Apex*.—Acute.
*Base*.—Cuneate.
*Margin*.—Entire.
*Length*.—0.3 cm.
*Width*.—0.1 cm.
*Color*.—Upper surface: Color is hidden. Lower surface: RHS 147C (Yellow-green).
*Surface texture*.—Upper surface: Hidden. Lower surface: Glabrous.
Reproductive organs: None observed.
Seed production: None observed.
Disease/pest resistance: None observed.
Temperature tolerance: High heat resistance.

COMPARISON WITH PARENTAL LINES AND KNOWN VARIETY

'Pearls Ginga Way' is a distinct variety of *Gypsophila* and is distinguished from its parents as described in Table 1:

TABLE 1

Comparison with Parental Lines

| Trait | Variety 'Pearls Ginga Way' | Female parent 'BL-MD-F-56' | Male parent 'BL-MD-M-189' |
|---|---|---|---|
| Heat resistance | High | High | Low |
| Need for supplemental light | Low | Medium | Low |

'Pearls Ginga Way' is a distinct variety of *Gypsophila* and is most similar to the *Gypsophila* commercial line 'Perfecta' (patent status unknown). Differences between the two varieties are described in Table 2:

TABLE 2

| Comparison with Similar Variety | | |
|---|---|---|
| Trait | Variety 'Pearls Ginga Way' | Commercial line 'Perfecta' |
| Flowering period | Early | Late |
| Need for supplemental light | Low | Very high |

I claim:

1. A new and distinct variety of *Gypsophila* plant named 'Pearls Ginga Way' as shown and described herein.

* * * * *